United States Patent [19]

Brown-Skrobot et al.

[11] Patent Number: 5,466,685

[45] Date of Patent: Nov. 14, 1995

[54] INHIBITION OF EXPRESSION OF BETA-LACTAMASE USING ESTERS OF FATTY ACID ALCOHOLS

[75] Inventors: Susan Brown-Skrobot, Hamilton, N.J.; Richard P. Novick; Steven J. Projan, both of New York, N.Y.

[73] Assignee: Johnson & Johnson, New Brunswick, N.J.

[21] Appl. No.: 61,222

[22] Filed: May 13, 1993

[51] Int. Cl.$^6$ .................. A61K 31/43; A61K 31/22; A61K 31/225; A61K 31/20

[52] U.S. Cl. .................. 514/199; 514/546; 514/547; 514/558; 514/560

[58] Field of Search .................. 514/547, 558, 514/560, 546, 199

[56] References Cited

PUBLICATIONS

Biosis Abstract of Journal of Antibiotics. (1981).
Biosis Abstract of Journal of Food Prot. (1992).

*Primary Examiner*—Zohreh Fay
*Attorney, Agent, or Firm*—Hopgood, Calimafde, Kalil & Judlowe

[57] ABSTRACT

A class of chemical compounds comprising fatty acid ester derivatives used to inhibit beta-lactamase production by infectious bacteria. These inhibitors have been found to retard the resistance of certain strains of bacteria to beta-lactam antibiotics, such as penicillin, by interfering with the transcription of the beta-lactamase gene and precluding expression of beta-lactamase. In accordance therewith, these inhibitors permit effective treatment of infections of otherwise resistive bacteria with antibiotics.

20 Claims, 2 Drawing Sheets

INHIBITION OF EXPRESSION OF BETA-LACTAMASE USING ESTERS OF FATTY ACID ALCOHOLS

This invention relates to the chemotherapy of bacterial infections whereby a class of fatty acid ester derivatives can be utilized as inhibitors of beta-lactamase production.

BACKGROUND OF THE INVENTION

1. Description of the Prior Art

Beta-lactam antibiotics, such as penicillin, methicillin, amoxicillin and the like, have been used for many years in battling bacterial infections in humans. After repeated exposure to this type of antibiotic, however, many bacterial strains have become resistant to these antibiotics and now render them ineffective in treating infections. The medical and scientific community believes that bacterial resistance to beta-lactam antibiotics can usually be attributed to the ability of these bacteria to produce beta-lactamase, an enzyme that cleaves the chemical structure of the beta-lactam antibiotics.

Researchers have, therefore, approached this problem by searching for beta-lactamase inhibitors that will prevent the action of beta-lactamase and permit this class of antibiotics to remain active in treating bacterial infections. Some of these beta-lactamase inhibitors are antibacterial; some act synergistically with beta-lactam antibiotics to increase their effectiveness.

For example, U.S. Pat. No. 4,340,539 (Gottstein), entitled "Derivatives of 6-bromo Penicillanic Acid" states that 2-B-chloromethyl-2a-methylpenam-3a-carboxylic acid sulfone and salts and esters thereof are potent inhibitors of beta-lactamases. The patent states that the active derivatives of 6-bromo penicillanic acid, in conjunction with ceforanide and amoxicillin, prevent the destruction of these beta-lactam antibiotics and permit continued antibacterial activity. The active material was demonstrated to have very weak antibacterial activity by itself.

R. Baltzer, et al., in their article "Mutual ProDrugs of B-Lactam Antibiotics and B-Lactamase Inhibitors," J. Antibiotics 33(10), 1183–1192 (1980) describes the combination of a beta-lactam antibiotic with a beta-lactamase inhibitor in a single molecule functioning as a pro-drug for the two active components. A beta-lactamase inhibitor, penicillanic acid sulfone, was combined with ampicillin and mecillinam. The article states that, in humans, these esters are absorbed from the gastrointestinal tract and, after absorption, are hydrolyzed with liberation of the active components.

U.S. Pat. No. 4,377,590 (Myers), entitled "Derivatives of Ampicillin and Amoxicillin with Beta-Lactamase Inhibitors" describes certain antibiotics having beta-lactamase inhibitors. These antibiotics contain a beta-lactam ring, as well as a carboxy group located on either the amino group of ampicillin, the amino group of amoxicillin, or the phenolic hydroxy group of amoxicillin.

European Patent Publication EP 0023 093 A1 (Harbridge), entitled "Penicllanic Acid Derivatives, Their Preparation and Use in Pharmaceutical Compositions" relates to pharmaceutical compositions containing penicillin or cephalosporin. The publication states that a class of penicillanic acid derivatives having antibacterial activity possess the ability to enhance the effectiveness of penicillin and cephalosporins.

British Patent No. 1,573,503 (Cherry, et al.), entitled "Ethers of (2)-hydroxy-ethylidene-clavam-(3)-carboxylic acid—Useful Antibiotics, Beta-lactamase Inhibitors and Intermediates" relates to ethers of clavulanic acid and their salts and esters. These compounds can be utilized as antibiotics or as beta-lactamase inhibitors. The patent states that these compounds have some antibiotic activity and are stable to the action of beta-lactamases. The patent also states that the compounds inhibit beta-lactamase enzymes.

WO 9117995 (Altamura, et al.) describes penem dithiocarbamate derivatives as beta-lactamase inhibitors for use of antibacterial agents and antibiotics. EP 212404 (Cooke, et al.) describes 2-phenyl-2-penem-3-carboxylic acid derivatives as being antibacterial agents and antibiotics. WO 8700525 (Broom, et al.) describes 6-heterobicyclic-methylene-penem-3-carboxylic acid compounds which are both antibacterial and possess beta-lactamase inhibitory activities.

Thus, research activities to date in the area of retaining the activity of beta-lactam antibiotics have focused on efforts to neutralize or inactivate beta-lactamase enzymes after they are formed. There has been little or no attention directed to preventing the formation of beta-lactamase enzymes by any means.

Of course, the ability to inhibit the formation of beta-lactamase enzymes is extremely desirable as this process would permit a larger proportion of beta-lactam antibiotics to be effective, without interference from the beta-lactamase enzymes.

SUMMARY AND OBJECTS OF THE PRESENT INVENTION

Thus, it is an object of this invention to provide a means for preventing the formation of beta-lactamase enzyme by bacteria.

It is a further object of this invention to provide a method by which to render bacteria sensitive to beta-lactam antibiotics.

Additional objects of this invention will become evident in accordance with the following discussion.

In accordance with the present invention, it has been discovered that certain esters of polyhydric aliphatic alcohols and fatty acids unexpectedly inhibit bacterial production of beta-lactamase. It is believed that such esters interfere with the transcription of the beta-lactamase blaZ gene and hence the expression of betalactamase enzyme by *Staphylococcus aureus* bacteria (hereinafter, "*S. aureus*"). Esters for this purpose are formed from fatty acids with eight to eighteen carbon atoms and polyhydric alcohols, wherein said ester has at least one hydroxyl substituent on its aliphatic alcohol residue. These esters are used in conjunction with beta-lactam antibiotics. Preferably, monoesters and diesters or mixtures of monoesters and diesters of a polyhydric aliphatic alcohols and a fatty acid having from eight to eighteen carbon atoms are used.

We theorize that when the compositions of this invention contact bacterial cells, they adversely affect the signal transduction function of the cell, thus inhibiting the expression of beta-lactamase at the level of transcription in the bacteria. In the case of beta-lactamase production in Staphylococci, the method of production is believed to be by a signal transduction pathway as described in *Bacillus licheniformis* by Y. Zhu, S. Englebert, B. Joris, J. M. Ghusen, T. Kobayashi and J. O. Lampen, in an article entitled "Structure, Function and Fate of the blaR signal transducer involved In Induction of Beta-lactamase In *Bacillus licheniformis*" in J. Bacteriology, Oct. 1992.174 (19), p. 6171–8. This pathway is analogous in Staphylococci based on amino acid similarity as reported by Wang, et al., Nucleic Acids Review, Vol. 19, p. 4000, 1991.

In general, signal transduction is the process by which gene expression is regulated in response to environmental signals. The bacterial cell often must adjust to changes in its external environment. In order to adjust to these changes, bacteria may have to respond by expressing a particular gene or group of genes or alternatively, turning off the expression of a gene or a group of genes. Therefore, the cell must have a means by which information about its environment is transmitted from the outside of the cell to the inside of the cell, accomplished by a process which is referred to as "signal transduction".

The signal which triggers beta-lactamase production in Staphylococci is beta-lactam-containing compounds such as penicillin. Under normal circumstances, beta-lactamase is not manufactured by the bacteria. The bacteria's failure to manufacture this compound under normal circumstances can be attributed to the inhibition of expression of the gene which encodes this protein (blaZ), i.e., the prevention of transcription of the gene. It is thought that BlaI inhibits the blaZ gene.

When bacteria are exposed to a beta-lactam compound, the beta-lactam compound becomes attached to the bacterial cell transmembrane receptor protein (BlaR1). The attachment to the BlaR1 protein initiates a cascade of events which are as yet not wholly understood, but which result in relieving the transcriptional inhibition of the blaZ gene by the BlaRI protein.

Signal transduction has historically been reported not only in *Bacillus licheniformis* but in *Salmonella typhimurium* as well, (K. Hannary, et al., "TonB Protein of *Salmonella Typhimurium* A Model for Signal Transduction Between Membranes," J. Mol. Biol. (1990) 216, 897–910. This article proposes a model whereby TonB serves as a "mechanical" linkage that acts as a means of coupling energy to outer membrane transport processes. This mechanism as described by Hannary, et al. has implications for signal transduction within and between proteins. This work was accomplished using TonB—beta-lactamase fusions.

In the article "Coordinate Regulation of Beta-lactamase Induction and Peptidoglycan Composition by the amp Operon," (E. Tuomanen, et al., Science, Vol. 251, p. 201–203 (1991), the authors suggest that beta-lactamase induction and modulation of the composition of the cell wall share elements of a regulatory circuit that involves AmpD. *E. coli* requires AmpD to respond to extracellular signalling by amino acids and this signal transduction system may regulate peptidoglycan composition in response to cell wall turnover products.

Previous signal transduction studies have focused predominantly on altering and/or blocking specific receptor sites on the trans-membrane receptors. However, the compositions of the present invention apparently affect signal transduction through the cell membrane in a non-specific manner and block several signal transduction pathways simultaneously. Specifically, the compositions of this invention inhibit transcription of the blaZ gene, thereby inhibiting production of blaZ messenger RNA ("mRNA"). This, in turn, precludes the translation of the information necessary to make the beta-lactamase protein. The result of this phenomenon is that the bacterial cell produces no beta-lactamase and, therefore, remains susceptible to beta-lactam antibiotics such as penicillin, methicillin, amoxicillin and the like.

The fatty acid portion of the aforementioned monoesters and diesters may, preferably, be derived from caprylic, capric, lauric, myristic, palmitic and stearic acids, which are saturated fatty acids whose chain lengths, respectively, are C8, C10, C12, C14, C16 and C18. The fatty acid portion of the aforementioned monoesters and diesters may be derived as well from unsaturated fatty acids having carbon chain lengths also ranging from C8 to C18. One example of such unsaturated fatty acids is oleic acid. Most preferably, the fatty acid is lauric acid, a saturated fatty acid whose chemical formula is $C_{11}H_{23}COOH$.

As used in this specification and the appended claims, the term "aliphatic" has the meaning usually accorded it in the field of organic chemistry, i.e., "aliphatic" refers to organic compounds characterized by straight or branched chain arrangement of the constituent carbon atoms.

As used in this specification and the appended claims, the term "polyhydric" refers to the presence in a chemical compound of at least two hydroxyl (OH) groups. Thus, a polyhydric aliphatic alcohol is one which has at least two hydroxyl groups and in which the carbon backbone is either straight or branched.

Polyhydric alcohols suitable for forming monoesters and/or diesters for use in the practice of the present invention are 1,2-ethanediol; 1,2,3-propanetriol(glycerol); 1,3-propanediol; 1,4-butanediol; 1,2,4-butanetriol and the like. The preferred polyhydric aliphatic alcohol for forming monoesters and diesters for use in the compositions of this invention is 1,2,3-propanetriol, commonly called glycerol, whose formula is $HOCH_2CH(OH)CH_2OH$.

Preferably, the esters which are useful in the practice of this invention have at least one hydroxyl group associated with their aliphatic alcohol residue. Thus, it will be understood that the monoester of 1,2-ethanediol and one of the aforementioned fatty acids may be used in the practice of this invention because said ester, whose general formula is:

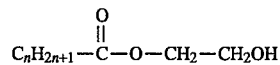

has at least one hydroxyl group (i.e., the hydroxyl group at the far right-hand side of the structural formula shown above) in that portion of the ester derived from the aliphatic alcohol 1,2-ethanediol. On the other hand, it will be understood that the diester of 1,2-ethanediol and one of the aforementioned fatty acids are preferably not used in the practice of this invention because said ester, whose general formula is:

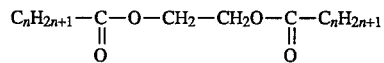

does not have at least one hydroxyl group in that portion of the ester derived from the 1,2-ethanediol.

The monoester of glycerol and one of the designated fatty acids is particularly useful in the practice of this invention because that ester has two hydroxyl groups associated therewith which are derived from the glycerol. The diester of glycerol and one of the designated fatty acids may also be used because that ester will have one hydroxyl group associated therewith which is derived from the aliphatic alcohol glycerol. Indeed, blends of glycerol monolaurate and glycerol dilaurate have been found to be useful in the practice of this invention. It will be understood that the triester of glycerol and one of the designated fatty acids is not useful in the practice of this invention because that ester does not have at least one hydroxyl group in the portion thereof which is derived from the aliphatic alcohol, i.e., glycerol.

Preferred esters for use in the practice of this invention are glycerol monolaurate, glycerol dilaurate and mixtures thereof.

BRIEF DESCRIPTION OF THE DRAWINGS

The foregoing features of the present invention may be more fully appreciated in the context of a detailed discussion thereof taken in conjunction with associated Figures thereto, of which.

DESCRIPTION OF THE INVENTION

Figure 1:
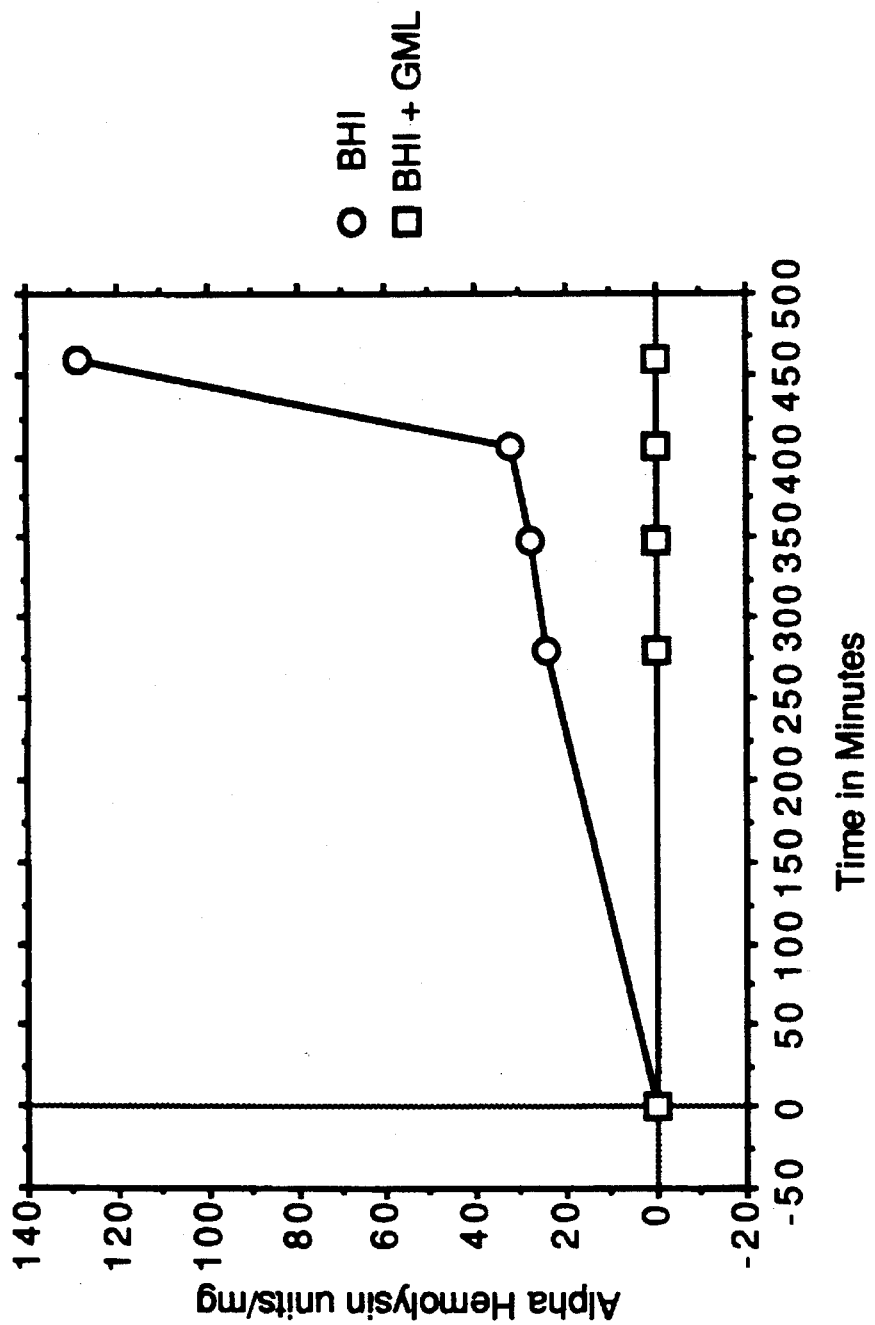
FIG. 1 depicts a graph representing direct tests for the inhibition of toxin production in conjunction with a preferred composition of this invention.

In the course of investigating the mechanism by which glycerol monolaurate ("GML") and its related compounds prevents the formation of TSST-1 toxin by S. aureus, as set forth in U.S. Continuation-in-Part patent application Ser. No. 717,168, entitled "Additives To Tampons", filed Jun. 17, 1991, corresponding to parent U.S. patent application Ser. No. 343,965, filed Apr. 27, 1989, it was unexpectedly found that placing a fatty acid ester compound according to this invention in contact with beta-lactamase-producing S. aureus inhibited the production of beta-lactamase in the presence of a beta lactam antibiotic, i.e., the signal that prompts the bacteria to produce beta-lactamase.

Three different pathways regulating exoprotein production in S. aureus are known or thought to involve transmembrane signaling. Two of these are global regulator pathways, namely: (1) agr (Kornblum, et al., "Molecular biology of the staphylococci," VCH Publishers, New York, 1990 and Morfeldt, et al., Mol. Gen. Genet., Vol. 211, p. 435, 1988) and (2) a post exponential phase signal (Vendenesch, et al., J. Bacteriol., Vol. 173, p. 6313, 1991). These global regulators are jointly required for the transcriptional activation of many exotoxin genes. The third pathway is the classical beta-lactamase induction pathway (Novick, J. Gen. Microbiol., Vol. 33, p. 121, 1963; Grossman, et al., Febs. Lett., Vol. 246, p. 83, 1989; Grossman, et al., Nucleic Acids Res., Vol. 15, p. 6049, 1987; Wang, et al., Nucleic Acids Res., Vol. 19, p. 4000, 1991, Wang, et al., J. Bacteriol., Vol. 169, p. 1763, 1987).

Agr activation is thought to involve signal transduction, on the basis of a resemblance between the predicted products of two of the agr genes, agrA and agrB, and the two components of the classical signal transduction pathways in bacteria (Kornblum, et al., 1990). The activating signal is not known, however, nor has transmembrane signalling been demonstrated for this system. The temporal signal is known, thus far, only as a physiological signal that is independently required for post exponential phase activation of exotoxin gene transcription. Beta-lactamase is indifferent to either of these global systems.

The best understood of the three systems is beta-lactamase induction, a bona fide signal transduction pathway. This pathway is activated by the binding of a beta-lactam structure to the transmembrane penicillin binding protein, BlaR1, conserved among gram positive bacteria (Wang, et al., 1991). This binding initiates a signal which ultimately relieves repression of the beta-lactamase promoter by BlaI, a classical repressor (Grossman, et al., 1989). Relieving the repression permits the formation of beta-lactamase.

Direct tests for the inhibition of signal transduction by the most preferred fatty acid ester, glycerol monolaurate ("GML"), were performed on the agr and beta-lactamase systems. These tests revealed that GML had no significant effect on the activation of agr transcription, whereas it completely blocked the induction of beta-lactamase. A graph of these test results is set forth in FIG. 2.

Moreover, this latter effect was specific for induction, as GML had no effect on the constitutive synthesis of beta-lactamase by blaI mutants. Preferably, in order to obtain the full effect of GML, the inhibitor (GML) should be added at least thirty minutes prior to the inducer (antibiotic). If the two were added simultaneously, only partial inhibition was seen. Although these results implicate transmembrane signal transduction as the target of GML inhibition of beta-lactamase induction, they do not reveal the particular target for exotoxin inhibition. A possible clue can be gleaned from experiments similar in nature to that shown in FIG. 1, in which GML inhibition of alpha-hemolysin synthesis was demonstrated. In particular, the residual alpha-hemolysin synthesis seen with an agr⁻ mutant was inhibited as fully as that seen with an agr⁺ wild type (not shown). This result is consistent with the implication that the GML-sensitive step in exotoxin synthesis is not agr and it indicates either that the temporal signal is the target or that there is some other unknown exotoxin regulation system or systems regulating exotoxin synthesis.

The inventors hypothesize that GML and its related fatty acid esters of polyhydric alcohols may inhibit signal transduction by intercalating into the cytoplasmic membrane and subtly modifying membrane structure so as to interfere with the conformational shifts in the structure of transmembrane proteins by which signals are projected through membranes. It is also possible that GML inhibits ligand binding. Effects on cytoplasmic elements of the signal transduction pathway are less likely because of the nature of the inhibitor.

EXAMPLE

Brain Heart Infusion ("BHI") Broth (Difco) was used as a growth medium. Glycerol monolaurate (Monomuls 90 L-12, manufactured by Henkel Corporation) was prepared at a concentration of 1% w/v in 95% ethanol. Cultures to be used as inocula were grown at 37° C. overnight without shaking in a 300 ml baffled, side arm, shaker flask having a volume of 10 ml. Ten ml of additional medium was added to the culture and the flasks were shaken at 240 rpm for one hour. The resulting, exponential phase culture was then subcultured by addition of 1.0 ml into 20 ml total in a side arm, 300 ml shaker flask and frown at 37° C. with shaking at 240 rpm. Growth was monitored turbidimetrically using a Klett-Sumerson photoelectric colorimeter with a green filter. The S. aureus strains used were as follows: RN11 is a derivative of S. aureus strain NTCC 8325 carrying pI258 (a naturally occurring beta-lactamase plasmid). Beta-lactamase production is inducible in this strain. RN24 is similar to RN11 except that the resident plasmid in RN24 is a mutant pI258 which has a mutation in the blaI gene rendering the strain a constitutive, high level producer of beta-lactamase.

Beta-lactamase producing S. aureus strains RN11 (inducible) and RN24 (constitutive) were grown in Brain Heart Infusion Broth as described above. Cells in log phase were subcultured 1:20 at time zero. Four separate RN11 cultures were followed and beta-lactamase production monitored and recorded as set forth in FIG. 2.

1. A culture grown without GML (represented by a circle);

2. A culture grown without GML induced at 75 minutes of growth with 4 µg/ml of carboxybenzyl aminopenicillanic acid (CBAP), a gratuitous inducer of beta-lactamase (represented by a square);

3. A culture grown with GML (conc.: 20 µg/ml) added at time zero and induced with CBAP at 75 minutes of growth (represented by a triangle);

4. A culture grown with GML (conc.: 20 µg/ml) and CBAP added simultaneously at 75 minutes of growth (represented by a diamond); and 5. A fifth culture with the constitutive blaI mutant of pI258 (RN24) was grown in the same manner as RN11 with GML (conc.: 20 µg/ml) added at time zero and CBAP added at 75 minutes (represented by a plus sign).

Samples were taken at the indicated time points and beta-lactamase activity was determined as described in C. H. O'Callaghan, et al., Antimicrob. Agents Chemother. 1, 283 (1972) and normalized to total cell mass.

Figure 2:
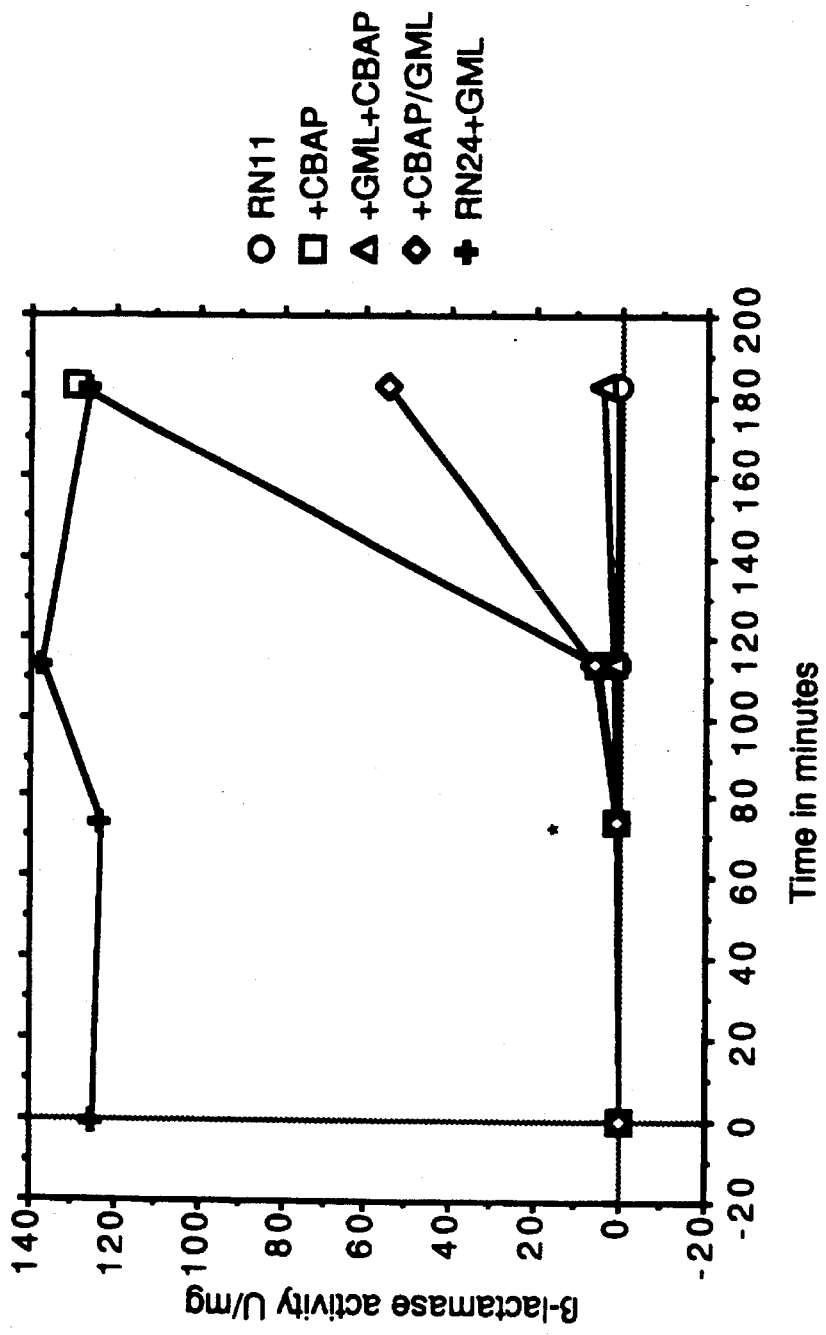
FIG. 2 depicts a graph demonstrating the effect of a preferred composition of this invention upon the production of betalactamase by S. aureus bacteria.

The results of this example are depicted graphically in FIG. 2. Direct tests for GML inhibition were performed on the agr and beta-lactamase systems and these revealed that GML had no significant effect on the activation of agr transcription (not shown). However, GML completely blocked the induction of beta-lactamase. Moreover, this latter effect was specific for induction as GML had no effect on the constitutive synthesis of beta-lactamase by blaI mutants. It should be noted that the full effect of GML was seen only if the inhibitor was added at least 30 minutes prior to the inducer. If the two were added simultaneously, only partial inhibition was seen. Although these results implicate trans-membrane signal transduction as the target of GML inhibition, they do not reveal the particular target for exotoxins.

FIG. 2, therefore, shows that when GML is added to a culture of a strain of Staphylococcus aureus, which inducibly produces beta-lactamase prior to addition of an inducer of beta-lactamase (CBAP—carboxybenzyl aminopenicillanic acid) that culture is inhibited for production of beta-lactamase. This result is depicted by the triangle. Addition of both GML and inducer simultaneously gives an intermediate level of inhibition, as shown by the diamonds. Addition of CBAP to a culture that is not treated with GML gives "full induction," as depicted by the open boxes. Failure to add inducer also results in no production of beta-lactamase, as depicted by the open circles. A culture defective in the beta-lactamase inhibitor gene BlaI produces beta-lactamase constitutively (i.e., at all times) and is not inhibited by GML, as indicated by the plus signs. Thus, we conclude that GML is acting at the level of signal transduction to prevent the induction of the transcription of beta-lactamase.

The in vivo activity of a beta-lactam antibiotic in combination or in conjunction with a fatty acid ester of glycerol is suitable for the control of bacterial infections in mammals including humans. They are administered orally, parenterally or transdermally, by infusion, or in combinations thereof. These compounds are useful in the control of infections caused by susceptible bacteria in human and animal subjects.

When the active compound combination of this invention is administered and comes into contact with susceptible bacteria, the fatty acid ester of glycerol or salts of fatty acid esters of a glycerol should inhibit the ability of the bacteria to produce beta-lactamase, thus leaving the beta-lactam antibiotic active to kill the susceptible bacteria. Thus, the compounds specified herein can be utilized in a 1:1 mixture or equally effective concentration combination of the fatty acid ester of glycerol to beta-lactam antibiotic. Final effective concentration of fatty acid ester of glycerol of 3–30 µg/ml and standard administered dose of beta-lactam antibiotic from 500 to 4000 mg or an equally effective dose. The beta-lactam antibiotic should be utilized in an amount effective to provide antibiotic activity to the person to whom it is administered.

When using an antibacterial compound combination of this invention in a mammal such as man, the compound combination comprising the fatty acid ester of glycerol and the beta-lactam antibiotic, either compound could be administered alone or mixed with pharmaceutically-acceptable carriers or diluents. Said carrier or diluent is chosen on the basis of the intended mode of administration. For example, when considering the oral mode of administration, a beta-lactam antibiotic plus fatty acid ester of glycerine can be administered in the form of tablets, capsules, lozenges, syrups, elixirs, aqueous solutions and/or suspensions and the like in accordance with standard pharmaceutical practice. The proportional ratio of active ingredient to carrier will depend on the chemical nature, solubility and stability of the active ingredient as well as the dosage contemplated. Another aspect of such formulations which should be taken into account is whether the compounds used therein are hydrolyzed or digested by various enzymes in the body.

For parenteral administration, which includes intramuscular, intraperitoneal, subcutaneous and intravenous use, sterile solutions of the active ingredients are usually prepared, and the pH of the solutions are suitably adjusted and buffered. For intravenous use, the total concentration of solutes should be controlled to render the preparation isotonic.

A third mode of administration is in a pharmaceutically acceptable carrier, with the active ingredient administered transdermally.

The antibiotic fatty acid ester combinations of this invention are of use in human and animal subjects and the daily dosages to be used will not differ significantly from other, clinically-used beta-lactam antibiotics such as penicillin, methicillin, amoxicillin, cephalosporin, oxacephalosporin, carbacephalosporin, carbapenem, penem, monobactam, and clavam. The prescribing physician will ultimately determine the appropriate dose for a given human subject and this can be expected to vary according to the age, weight, and response of the individual patient as well as the nature and severity of the patient's symptoms.

The above-described arrangement is merely illustrative of the principles of the present invention. Numerous modifications and adaptations thereof will be readily apparent to those skilled in the art without departing from the spirit and scope of the present invention.

What is claimed is:

1. A method for inhibiting beta-lactamase expression in bacteria, comprising the step of:

exposing said bacteria to a composition comprising an ester formed from a fatty acid and a polyhydric aliphatic alcohol, wherein said ester is supplied in said composition in quantities sufficient to inhibit beta-lactamase expression in said bacteria.

2. The method of claim 1, wherein said composition further comprises a pharmaceutically acceptable carrier.

3. The method of claim 2, wherein said composition further comprises a beta-lactam antibiotic.

4. The method of claim 3, wherein said beta-lactam antibiotic is selected from the group consisting of amoxicillin, ampicillin, methicillin and penicillin.

5. The method of claim 1, wherein said fatty acid is selected from the group consisting of caprylic acid, capric acid, lauric acid, myristic acid, palmitic acid and stearic acid.

6. The method of claim 5, wherein said fatty acid is lauric acid.

7. The method of claim 1, wherein said polyhydric aliphatic alcohol is selected from the group consisting of 1,2-ethanediol, 1,3-propanediol, 1,2,3-propanetriol, 1,4-butanediol and 1,2,4-butanetriol.

8. The method of claim 7, wherein said polyhydric aliphatic alcohol is 1,2,3-propanetriol (glycerol).

9. The method of claim 1, wherein said ester is glycerol monolaurate.

10. A method according to claim 1, wherein said ester is selected from the group consisting of monoesters, diesters, salts of monoesters and salts of diesters.

11. A method according to claim 1, wherein said ester has at least one hydroxyl group associated with its aliphatic alcohol residue.

12. The method of claim 1, wherein said inhibition of beta-lactamase expression is via inhibition of signal transduction for the transcription of said beta-lactamase.

13. A method for inhibiting beta-lactamase expression in bacteria, comprising the steps of:

a. forming a composition of a monoester made from a fatty acid and a polyhydric alcohol, and a diester formed from a second fatty acid and a second polyhydric aliphatic alcohol wherein said mono and diester include at least one hydroxyl group on the polyol residue, and b. exposing said bacteria to said composition in quantities sufficient to inhibit expression of beta-lactamase in said bacteria.

14. The method of claim 13, wherein said fatty acid is selected from the group consisting of caprylic acid, capric acid, lauric acid, myristic acid, palmitic acid, stearic acid and oleic acid.

15. The method of claim 13, wherein said polyhydric aliphatic alcohol is selected from the group consisting of 1,2-ethanediol, 1,3-propanediol, 1,2,3-propanetriol, 1,4-butanediol and 1,2,4-butanetriol.

16. The method of claim 13, wherein said monoester and said diester have at least one hydroxyl group associated with their aliphatic alcohol residues.

17. The method of claim 13, wherein said monoester is glycerol monolaurate and said diester is glycerol dilaurate.

18. The method of claim 13, wherein said composition further comprises a pharmaceutically acceptable carrier.

19. The method of claim 18, wherein said composition further comprising a beta-lactam antibiotic.

20. The method of claim 19, wherein said beta-lactam antibiotic is selected from the group consisting of amoxicillin, ampicillin, methicillin and penicillin.

* * * * *

UNITED STATES PATENT AND TRADEMARK OFFICE
CERTIFICATE OF CORRECTION

PATENT NO. : 5,466,685
DATED : November 14, 1995
INVENTOR(S) : Brown-Skrobot et al.

It is certified that error appears in the above-identified patent and that said Letters Patent is hereby corrected as shown below:

ON THE COVER PAGE:

Item: [73] Assignee:

delete " Johnson & Johnson, New Brunswick, N.J." and insert —Public Health Research Institute, New York, N.Y.— .

Signed and Sealed this

Fifth Day of November, 1996

Attest:

BRUCE LEHMAN

Attesting Officer

Commissioner of Patents and Trademarks